United States Patent
Silver et al.

(10) Patent No.: US 10,493,187 B2
(45) Date of Patent: *Dec. 3, 2019

(54) HIGHLY EFFICIENT BREASTPUMP AND SYSTEM FOR EXPRESSING BREASTMILK

(71) Applicant: MEDELA HOLDING AG, Baar (CH)

(72) Inventors: Brian H. Silver, Woodstock, IL (US); Sam Levey, Pittsburgh, PA (US); Carr Lane Quackenbush, Monson, MA (US); Beda Weber, Sins (CH); Etienne Furrer, Zug (CH); Daniela Wackerlin, Baar (CH)

(73) Assignee: MEDELA HOLDING AG, Baar (CH)

( * ) Notice: Subject to any disclaimer, the term of this patent is extended or adjusted under 35 U.S.C. 154(b) by 348 days.

This patent is subject to a terminal disclaimer.

(21) Appl. No.: 15/428,459

(22) Filed: Feb. 9, 2017

(65) Prior Publication Data
US 2017/0151380 A1 Jun. 1, 2017

Related U.S. Application Data

(62) Division of application No. 12/885,145, filed on Sep. 17, 2010, now Pat. No. 9,603,982.

(Continued)

(51) Int. Cl.
*A61M 1/06* (2006.01)
*A61M 1/00* (2006.01)

(52) U.S. Cl.
CPC ............ *A61M 1/06* (2013.01); *A61M 1/0072* (2014.02); *A61M 1/064* (2014.02); *A61M 1/066* (2014.02); *A61M 2202/0014* (2013.01)

(58) Field of Classification Search
CPC ........ A61M 1/06; A61M 1/064; A61M 1/066; A61M 1/068; A61M 1/062; A61M 1/0072;

(Continued)

(56) References Cited

U.S. PATENT DOCUMENTS

| 949,414 A | 2/1910 | Cunningham |
|---|---|---|
| 4,799,922 A | 1/1989 | Beer et al. |

(Continued)

FOREIGN PATENT DOCUMENTS

| EP | 1219833 A1 | 7/2002 |
|---|---|---|
| EP | 2127690 A2 | 12/2009 |

(Continued)

OTHER PUBLICATIONS

International Search Report for corresponding International Patent App. No. PCT/CH2010/000226, dated Jan. 4, 2011.

(Continued)

*Primary Examiner* — Matthew F Desanto
(74) *Attorney, Agent, or Firm* — McDonnell Boehnen Hulbert & Berghoff LLP

(57) ABSTRACT

The present invention provides a breastshield for use in a breastpumping system for expressing milk, the breastshield being of such a construction that substantially limits the amount of air between the breast/nipple and the breastshield surrounding the breast/nipple, and most preferably virtually eliminates any air at least in the area of the breast and nipple. In some embodiments, any air in the breastpumping system is substantially eliminated. With the amount of air limited, the mechanism used for generating the pressure difference in the breastshield (e.g., vacuum or negative pressure), such as a diaphragm pump, does not need to do as much work. Less energy is required for the expression of milk, and thus the size of pump used can be decreased, thereby reducing the overall cost of the device.

12 Claims, 10 Drawing Sheets

Related U.S. Application Data

(60) Provisional application No. 61/244,636, filed on Sep. 22, 2009.

(58) Field of Classification Search
CPC ............ A61M 1/1032; A61M 5/14593; A61M 5/14526
See application file for complete search history.

(56) References Cited

U.S. PATENT DOCUMENTS

| | | | |
|---|---|---|---|
| 4,857,051 A | 8/1989 | Larsson | |
| 4,929,229 A | 5/1990 | Larsson | |
| 5,601,531 A | 2/1997 | Silver | |
| 5,616,125 A | 4/1997 | Jelks | |
| 6,161,710 A | 12/2000 | Dieringer et al. | |
| 6,379,327 B2 | 4/2002 | Lundy | |
| 6,440,100 B1 | 8/2002 | Prentiss | |
| 6,461,324 B1 | 10/2002 | Schlensog | |
| 6,663,587 B2 | 12/2003 | Silver et al. | |
| 6,669,064 B2 | 12/2003 | Perricone | |
| 7,070,400 B2 | 7/2006 | Greter | |
| 7,094,217 B2 | 8/2006 | Fialkoff | |
| 7,223,255 B2 | 5/2007 | Myers et al. | |
| 7,238,165 B2 | 7/2007 | Vincent et al. | |
| 7,559,915 B2 | 7/2009 | Dao et al. | |
| 7,662,127 B2 | 2/2010 | Silver et al. | |
| 7,819,839 B2 | 10/2010 | Gillan | |
| 7,833,190 B1 | 11/2010 | Hall | |
| 8,118,772 B2 | 2/2012 | Dao et al. | |
| 8,568,350 B2 | 10/2013 | Schlienger et al. | |
| 9,603,982 B2 | 3/2017 | Silver et al. | |
| 9,956,331 B2 * | 5/2018 | Weber | A61M 1/0072 |
| 2003/0191433 A1 | 10/2003 | Prentiss | |
| 2004/0071572 A1 | 4/2004 | Greter | |
| 2004/0087898 A1 | 5/2004 | Weniger | |
| 2004/0181187 A1 | 9/2004 | Warburton | |
| 2005/0043677 A1 | 2/2005 | Kelly | |
| 2005/0154349 A1 | 7/2005 | Renz et al. | |
| 2005/0222536 A1 | 10/2005 | Silver | |
| 2006/0106334 A1 | 5/2006 | Jordan et al. | |
| 2006/0270973 A1 | 10/2006 | Chu | |
| 2007/0078383 A1 | 4/2007 | Tashiro et al. | |
| 2008/0039781 A1 | 2/2008 | Bjorge | |
| 2008/0090445 A1 | 4/2008 | Luzbetak et al. | |
| 2008/0146118 A1 | 6/2008 | Solberg et al. | |
| 2008/0171970 A1 | 7/2008 | Luzbetak et al. | |
| 2008/0243059 A1 * | 10/2008 | Yamashita | A61M 1/06 604/74 |
| 2008/0255503 A1 | 10/2008 | Quackenbush et al. | |
| 2008/0275386 A1 * | 11/2008 | Myers | A61M 1/06 604/74 |
| 2008/0287037 A1 | 11/2008 | Solberg | |
| 2009/0062731 A1 | 3/2009 | Keyong et al. | |
| 2009/0099511 A1 | 4/2009 | Sutrina et al. | |
| 2009/0124967 A1 | 5/2009 | Zucker-Franklin | |
| 2009/0264837 A1 | 10/2009 | Adahan | |
| 2010/0121263 A1 | 5/2010 | Farka | |

FOREIGN PATENT DOCUMENTS

| | | |
|---|---|---|
| JP | 2004-522890 A | 7/2004 |
| JP | 2008-538955 A | 11/2008 |
| KR | 2004-0051728 A | 6/2004 |
| SU | 1319 A1 | 9/1924 |
| WO | 96/22116 A1 | 7/1996 |
| WO | 99/44650 A1 | 9/1999 |
| WO | 02/102437 A2 | 12/2002 |
| WO | 2005/067997 A1 | 7/2005 |
| WO | 2006/117352 A2 | 11/2006 |
| WO | 2008/008781 A2 | 1/2008 |
| WO | 2008/057218 A2 | 5/2008 |
| WO | 2008/090386 A1 | 7/2008 |
| WO | 2008/137678 A1 | 11/2008 |

OTHER PUBLICATIONS

International Search Report for corresponding International Patent App. No. PCT/CH2010/000225, dated Jan. 12, 2011.
International Search Report for Int. App. No. PCT/US2010/049355 dated May, 16, 2011.
English Translation of the Int. Preliminary Report on Patetablity for Int. App. No. PCT/CH2010/000225, dated Apr. 12, 2012.
English Translation of the Int. Preliminary Report on Patetablity for Int. App. No. PCT/CH2010/000226, dated Apr. 12, 2012.

* cited by examiner

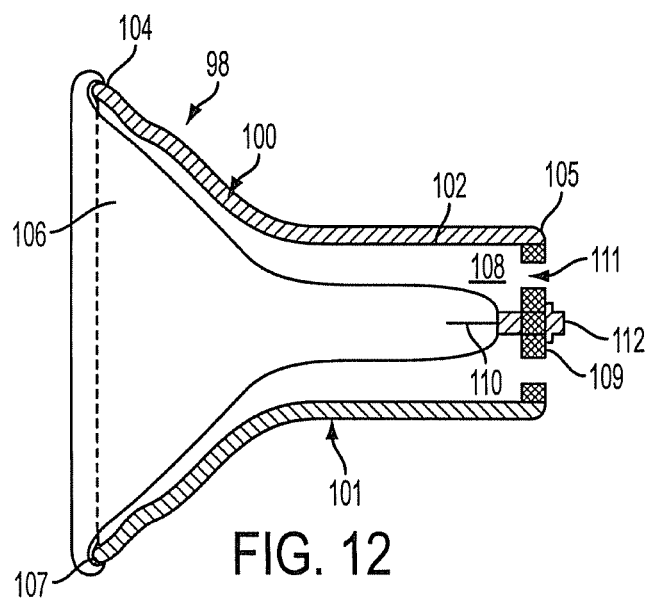
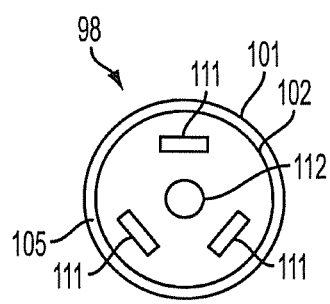
FIG. 12
FIG. 13
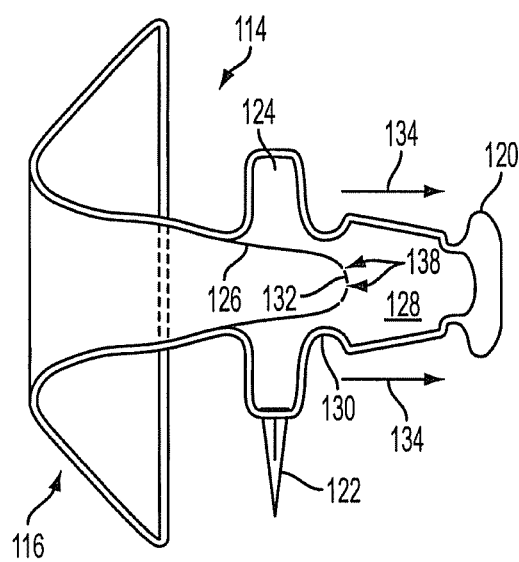
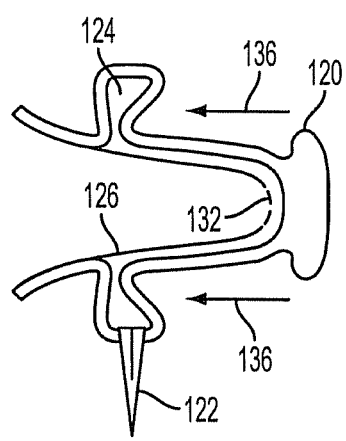
FIG. 14
FIG. 15A

HIGHLY EFFICIENT BREASTPUMP AND SYSTEM FOR EXPRESSING BREASTMILK

CROSS REFERENCE TO RELATED APPLICATIONS

The present application is a divisional of U.S. patent application Ser. No. 12/885,145, filed Sep. 17, 2010, which claims priority to provisional application Ser. No. 61/244,636 filed on Sep. 22, 2009. This application is also related to U.S. patent application Ser. No. 13/742,502, filed Jan. 16, 2013. The entire disclosure contents of these applications are herewith incorporated by reference into the present application.

FIELD OF THE INVENTION

The invention relates generally to breastmilk pumps, and particularly to an improved breastpump assembly for expressing mothers' milk, which in one significant aspect, substantially eliminates any "dead volume" in pumping, especially in the area of the breast and nipple.

BACKGROUND

Breastpumps are well known, and generally are comprised of breastshields (also referred to as hoods) that fit over the breast, a vacuum pump connected to the breastshield for generating an intermittent vacuum within the breastshield, and a receptacle for the milk that is pumped from the breast. Manually driven vacuum pumps are commonplace, as well as those that are driven by a motor (house current, battery, pneumatic, etc.).

The vacuum pumps of these devices intermittently generate a vacuum (or negative pressure) within the breastshield, with the breastshield covering the nipple and typically a substantial amount of the breast itself. The intermittent suction action of the pump serves to pull on the nipple, and so express milk, in an action that some have considered similar to suckling. The milk so extracted ordinarily flows from the breastshield into a collection container, e.g., a bottle, for storage and later use. A breastpump of the foregoing description is shown in U.S. Pat. Nos. 4,857,051, and 4,929,229, and reference thereto may be made for further detail on breastpumps in general. A recent advancement in these types of breastpumps is also disclosed in US Patent Publication 2008/0171970.

Breastshields typically have a funnel-shape, comprising a conical portion with a tubular extension, the latter sometimes referred to as the nipple tunnel. The nipple and surrounding breast are received in the conical portion, with the nipple often extending into the tubular extension. Under vacuum, the breast is pulled further into the breastshield, ordinarily with the nipple then being pulled into the tubular extension, with the surrounding breast thereby also typically being pulled further into the funnel.

A nursing mother's nipples may thus be forced against the wall of the nipple tunnel under vacuum. This may cause friction against the wall as the nipple moves deeper into the nipple tunnel. There can also be friction between the breast and the conical portion, as well as in the nipple tunnel. This is actually a back-and-forth movement under the intermittent vacuum, exacerbating the effects of the frictional engagement.

Researchers, particularly those working with Medela, have studied the manner in which infants breastfeed, and have come to seriously question the "conventional wisdom" on how a baby feeds from the breast. For instance, it appears that a vacuum instead of a stripping action is occurring during milk expression. Further, nipple placement is proximal to the hard/soft palate junction rather than at the junction. Ultrasound imaging shows that there is little to no air in the natural "system" when the infant is nursing. In other words, when the infant is latched onto the mother's breast, there is little to no air in the infant's mouth. The suckling action by the baby seems to radially compress as well as expand (or release some compression) the nipple; the nipple attempts to expand into the volume created as the baby's tongue moves away from the palate.

In contrast, in commercially available breastpumps used by mothers for expressing or extracting breastmilk for later use by the infant, air is present in the system, specifically in the breastshield into which the breast is placed. Once a mother's breast is in place, the pump must work not only to express the breastmilk from the breast but also must work to move the air in the system as well. This, understandably, affects the size of the pump, and the energy required to make the pump work.

Another observation of researchers is that, during nursing, the baby latches onto the mother's breast and the baby's tongue has continual contact and interacts with the nipple of the breast to bring about the flow of milk. In commercially available pumps, once the breast is inserted into the breast cup or shield, the vacuum generated by the pump typically pulls the breast further into the breastshield, ordinarily with the nipple then being pulled deeper into the tubular extension. The nipple tends to be more or less "free" within the nipple tunnel, except to the extent it may be pulled into contact with the nipple tunnel wall (or expands to fill the tunnel diameter because of the applied vacuum). When compared to nursing, the expression of milk with a breastpump of this conventional design can bring about some discomfort to the mother, and does not entirely duplicate the feel and conditions present in normal suckling.

Further, with the available breast pumps, a mother generally is in a substantially vertical position while pumping, and the bottle into which the breastmilk flows must be located in a position downwardly from the mother. This is because conventional breastpumps operate using gravity as the prime mover to move milk from the breastshield to the bottle. This limits the mother's activities while pumping; for example, she cannot recline to any great extent while pumping.

SUMMARY

Embodiments of the present invention provide a breastshield for use with a breastpump for expressing milk, the breastshield being of such a construction that substantially limits the amount of air between the breast/nipple and the breastshield surrounding the breast/nipple, and most preferably virtually eliminates any air at least in the area of the breast and nipple. With the amount of air limited, the mechanism used for generating the pressure difference in the breastshield (e.g., vacuum or negative pressure), such as a diaphragm pump, does not need to do as much work. Less energy is required for the expression of milk, and thus the size of pump used can be decreased, thereby reducing the overall cost of the device.

The vacuum pump can therefore be configured to be smaller and lighter, which means that it is in turn less conspicuous to onlookers. The mother can use the vacuum pump more discreetly. In addition, because of the lower energy, the vacuum pump is quieter during use, which in turn increases the comfort and discretion.

One aspect of the small working volume of the invention includes utilizing sensing of the vacuum pressure applied to the nipple and processing the vacuum level reading, as through a microprocessor control system, for example. The microprocessor then drives the pump in a manner to ensure the appropriate vacuum profile is produced at the nipple. This will allow the invention to perform consistently from mom to mom and will also allow for an improved reproduction of vacuum profiles of an infant. A vacuum regulator could similarly be used. Such sensing or regulation could further be useful in maintaining a baseline vacuum or minimum vacuum at the nipple, which remains throughout the pumping session.

Movement of the nipple can thereby be limited, and the amount of air in the system reduced or virtually eliminated, especially in embodiments of the present invention for the expression of milk including a baseline vacuum. A baseline vacuum would be one that is maintained during some or all of a pumping session, such that the pressure seen at the nipple does not return to ambient, but remains at, say, a pressure of approximately −20 to −50 mmHg, before returning to a greater vacuum during milk extraction. Reference can be made to U.S. Patent Publication No. 2008/0255503 entitled "Method and Apparatus for Minimum Negative Pressure Control, Particularly For Breastpump With Breastshield Pressure Control System," filed on Apr. 11, 2007, which is incorporated by reference herein in its entirety, for further detail on such "baseline vacuum."

Further, with the breastshield of the present invention, vacuum may act on a smaller portion of the mother's breast, indeed on the nipple alone, as compared to known breastshields. Specifically, the breastshield of the present invention in one aspect constrains the nipple of the breast, and provides contact surrounding a significant portion or substantially all of the nipple, more closely duplicating conditions in normal breastfeeding.

The reduction of air in the area of the nipple, or further in the entire system can range from substantially no air ("zero dead volume"), or substantially no air after initialization (i.e., air is largely or completely eliminated in the working volume after one or more initial cycles); or a small volume of air remains, but still achieving one or more of the inventive objectives. This reduction of air can consist of an initially larger opening which subsequently conforms more closely to the nipple to reduce the air volume around it. Embodiments include, but are not limited to, the use of inflating seals, self expanding seals, fit adjustment mechanisms, as well as custom fit openings.

In an embodiment of the invention a vacuum is applied just to the end of the constrained nipple. Embodiments for the constraint of the nipple include either longitudinal, radial, or both radial and longitudinal limitation to nipple movement. Such constraint will limit the expansion of the nipple from applied negative pressure, resulting in improved comfort. Again, as used herein, this "expansion" could be an extension of the nipple from its rest shape, or in the sense of going from a compressed condition to a less compressed condition.

Another attribute or aspect of the invention is providing embodiments that closely surround the nipple and adjacent breast with part of a lateral sidewall (or walls) of the breastshield that are designed to be reminiscent of the tongue of the baby. That is, this sidewall structure is then made to move radially relative to the breast/nipple. This in turn moves the breast/nipple outwardly (i.e., expanding it), which is believed to be much more like what an infant's suckling actually does.

Several embodiments of the invention include the use of low durometer materials to simulate the soft tactile feel and function of the inside of a baby's mouth.

As well, this invention comprises embodiments where a separate suction source or sources may be applied to the end of the nipple for the expression of milk. In this aspect the constraint of the nipple serves to provide the benefits of comfort and tactile sensation, as well as provide a sealing element at the base of the nipple to further reduce the working volume of air.

In an aspect of the invention, more of a radial force is applied to the nipple than a longitudinal force, i.e., the nipple is subjected to a force that tends to enlarge the nipple radially, and then compress or return the nipple as the breastshield returns to an initial condition. This expansion of the breastshield can be used to create the suction pressure to express milk, reducing or eliminating the need for a second vacuum source.

Several embodiments of the invention include an expansion of the nipple during the vacuum rise portion of a vacuum cycle. When the vacuum is returned to an ambient or baseline level, the nipple is relaxed or even somewhat compressed.

An embodiment of the invention includes not expanding the nipple beyond its natural diameter.

Another aspect of the invention is an apparatus and method for improved breastfeeding by compressing the nipple asymmetrically, i.e., out-of-round. In a conventional pump, the nipple is drawn into a structure (e.g., nipple tunnel) which has a circular cross-section. It is considered an advantage herein to provide a structure where the nipple is subjected to a radial force that presses it into a more elliptical cross-section.

In addition to the lateral or longitudinal constraint described above, an aspect of the invention includes the further constraint of the nipple from lateral movement, including utilizing a physical constraint of movement at the distal end of the nipple. The location of this physical end constraint can be adjusted to an individual. The end constraint may further consist of a porous cover to allow milk and pressure transfer through it, such as a porous membrane, valve, or orifice structure.

While an objective of the invention is to minimize the "dead volume," with some embodiments even substantially eliminating "dead volume" throughout the entire system, it is readily apparent that the invention described has advantages not limited to the foregoing, such that the system might have a large or typical air volume away from the proximal location of the nipple, but just include the elements of nipple constraint to gain the benefits of comfort and effective milk expression.

Embodiments of the invention can also readily utilize any of the nipple contact surfaces to provide a tactile stimulation to the nipple, further improving comfort and enhancing milk ejection. This includes the use of tactile features on the contact surfaces, and alternately includes driving of the contact surfaces with a force to apply a stimulation to the nipple, either in sync with or unrelated to the vacuum cycle.

In addition, due to the substantial elimination of air from the system of the present invention, the mother is not required to be in a substantially vertical position while expressing milk; further the container into which the expressed breastmilk flows does not need to be located downwardly with respect to the mother. An embodiment provides for a system which actively forces liquid to move, and is not reliant on gravity. The expressed milk moves through the breastpump assembly to the container provided, regardless of its location with respect to the mother. This provides flexibility for the mother in the type of activities in which she can participate while expressing milk. It also allows the breastpump assembly conduit structure, and even the container into which the expressed milk is collected, to be located other than downwardly with respect to the mother's breast. As well, the container may be of a type, such as an expandable container, that is normally closed or compressed and can be expanded by the expelled milk as the container is filled. As a result, the milk can be expressed independently of the relative orientation of the breastshield, the milk collecting container, and the vacuum pump with respect to one another. The mother may, for example, even express milk while lying down. This is particularly optimal in a "hands-free" embodiment since the mother may even bend down and in general move more freely.

Another embodiment of the invention has the mother's milk routed, at least in part, into the channel through which the vacuum, or working fluid, is initially operating on the breastshield. The milk thereby replaces the "air" (vacuum) in this part of the system, turning it from a pneumatic system to a hydraulic system. This is considered to increase the efficiency. That is, this reduces the work that the pump needs to do to achieve the effective vacuum level, and thus increases the efficiency of the system. A further salutary benefit is that the mother's own milk can now be used to warm the shield.

Another embodiment of the invention utilizes a sheath-like membrane which is emplaceable over a funnel-shaped or other breast-receiving shaped shield part, thereby forming a liner to the shield part. The sheath-like membrane is adapted to closely surround the nipple, achieving objectives of greatly eliminating air volume surrounding the breast/nipple and improved tactile sensation. The sheath-like membrane can also be made disposable, providing an additional benefit.

These as well as other aspects and advantages of the invention will become further apparent to those of skill in the art by reading the following detailed description, with reference where appropriate to the accompanying drawings. It should be understood that the embodiments described herein are intended to illustrate the invention by way of example only, and are not limiting.

BRIEF DESCRIPTION OF THE FIGURES

Exemplary embodiments of the invention are described herein with reference to the drawings, in which:

FIG. 12 is still a further embodiment of the inventive breastshield in sectional view;

FIG. 13 is a rear end view of the breastshield of FIG. 12;

FIG. 14 is another embodiment of the inventive breastshield in sectional view, shown in a first position;

FIG. 15A is a partial view of the embodiment of FIG. 14 in a second position;

DETAILED DESCRIPTION

Figure 1:
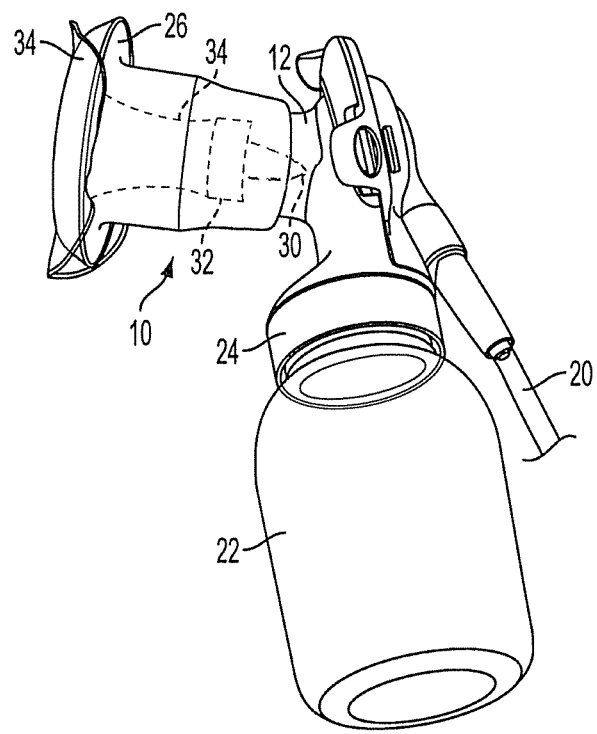
FIG. 1 is a perspective view of an embodiment of the present invention.

FIG. 1 depicts a first system for expressing breastmilk in accordance with the present invention. The system includes a breastshield 10 attached to a base 12. Base 12 is part of a breastpump assembly more particularly shown in US Patent Publication 2008/0171970, the disclosure of which is incorporated herein by reference. That assembly includes a vacuum pump which utilizes a barrier component (see FIG. 5) or diaphragm 14 that is enclosed in a clamshell-like chamber made of a front housing 18 and a rear housing 16. The barrier is reciprocated within the space of the housings 16, 18 by an intermittent vacuum from a vacuum source (not shown) which is connected via a tube 20 (see FIG. 1). Movement of the barrier downstream by the vacuum source conveys vacuum upstream by its movement (expanding the volume upstream).

Milk extracted in operation flows to a container 22 attached to a collar 24 which communicates with conduit structure within the breastshield assembly. Again, the details of this breastshield assembly and breastpump can be gleaned from the foregoing patent publication. As will be well appreciated, this embodiment using the foregoing pump of FIGS. 1-5, while substantially eliminating any residual air in the immediate vicinity of the nipple, as will be shortly described in detail, still will contain a volume of air on either side of the barrier (diaphragm), and especially in the tubing extending to the vacuum source. The present invention not only contemplates substantially eliminating the "dead volume" of air at the nipple, but in other embodiments (see, e.g., FIGS. 14, 15A, 15B and FIGS. 21-22), the virtual elimination of the "dead volume" in the entire system.

Figure 2:
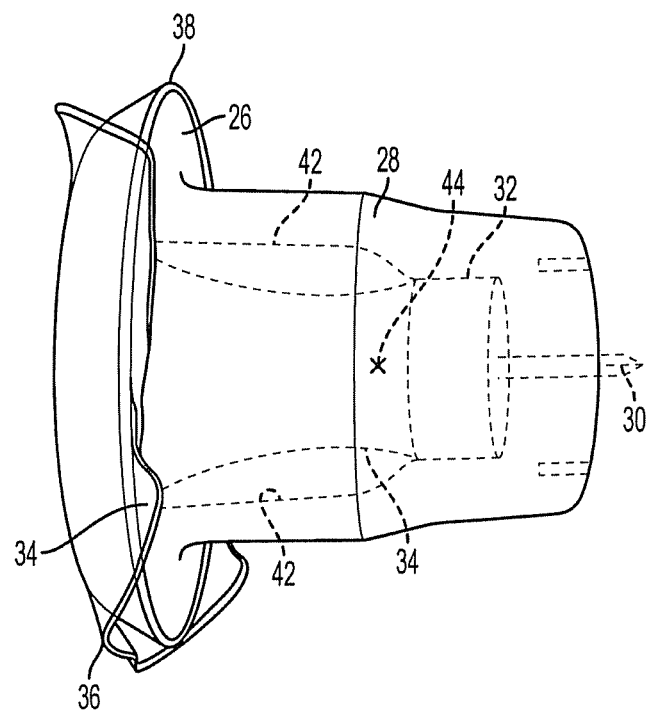
FIG. 2 is a side elevational view of the breastshield part shown in FIG. 1.
Figure 5:
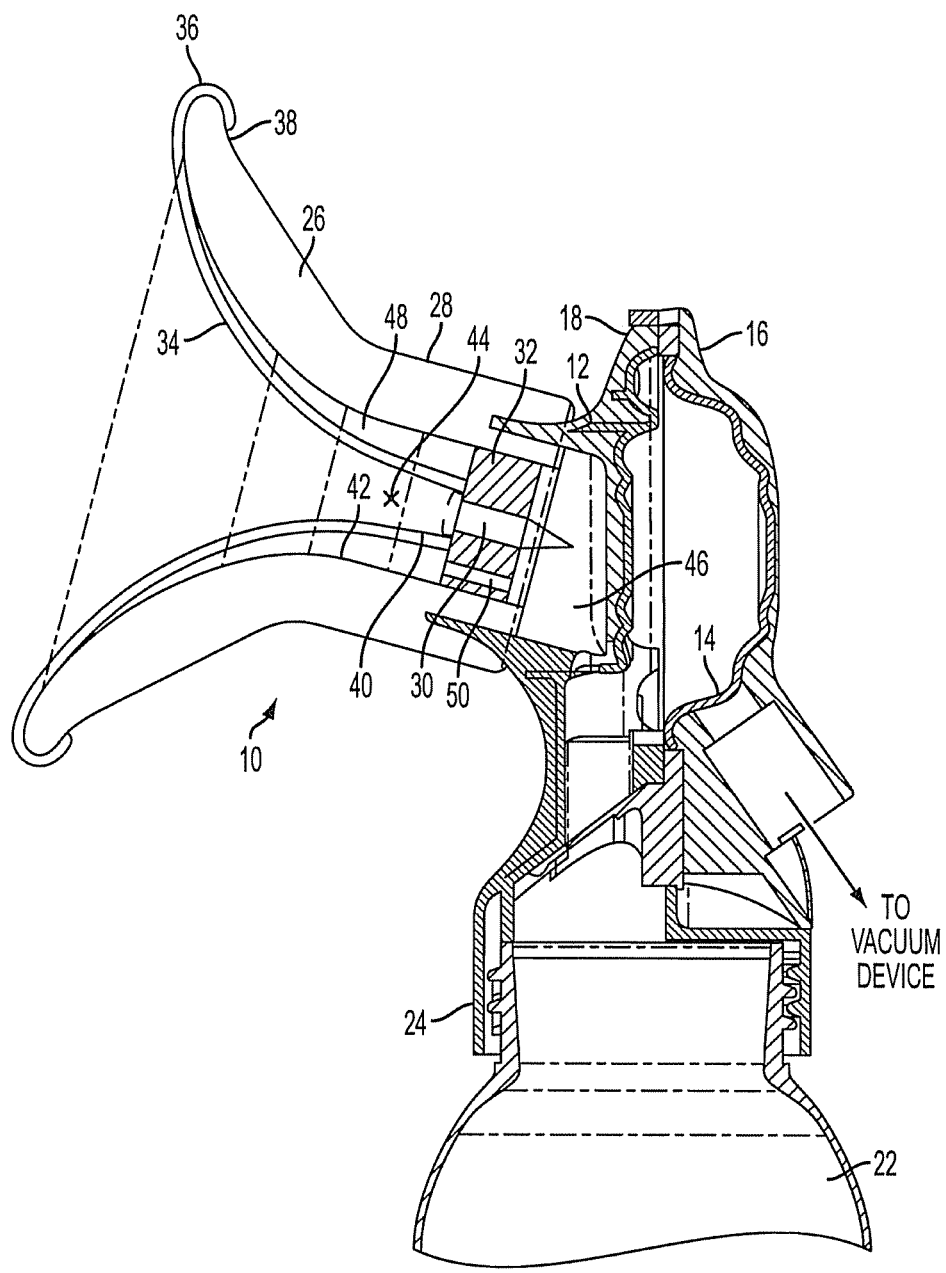
FIG. 5 is a sectional view in elevation of an embodiment like that of FIG. 1.

As can be seen in FIG. 1 and in further detail in FIGS. 2 and 5, the breastshield 10 includes a funnel or conical portion 26, a tubular extension or nipple tunnel 28 extending therefrom, and a valve 30 provided at the downstream end of the tubular extension 28. The terms funnel and conical are being used herein with reference to the more traditional shapes of breastshields, which are adapted to receive the nipple and surrounding breast therein. As is evident herein, however, the breast receptacles of many of the embodiments no longer employ a true "funnel" or "cone" geometric shape.

The lack of a large volume funnel accommodates a wide range of breast sizes and types and minimizes the potential dead volume in the funnel and nipple tunnel area. The valve 30 used in this version is a duckbill valve. It is mounted in a solid ring 32, which closes the end of the tubular extension 28.

The breastshield of the present invention is further provided with a sheath-like member 34, which functions in part as a liner for the funnel part of the breastshield 10 (portion 26 and nipple tunnel 28). The sheath member 34 has a rim part 36 that fits around and secures the widened mouth of the sheath member to the outer circumference of a rim 38 of the shield portion 26 (see FIGS. 3 and 4 in particular). Shield portion 26 and nipple tunnel 28 thereby form a frame for the sheath member 34.

The sheath member 34 is connected at its downstream end 40 about the upstream end of the duckbill valve 30, sealing around that valve on a downstream edge surrounding the valve. As can be seen in FIG. 5 in particular, the sheath member 34 is also somewhat funnel-like in shape, being placed into some stretched tension (i.e., taut) through the foregoing mounting arrangement. This serves to pull the sidewalls of the sheath member 34 away from the inner sidewall 42 of the breastshield 10 (much like stretching an unfilled balloon). The sheath receives the nipple of the breast in use, and snugly holds the nipple and some adjacent breast in a supple embrace. The sheath 34 is made of silicone rubber in a relatively thin thickness, again, much like a thick balloon. As can be seen from FIG. 4, the sheath can be easily removed from the breastshield, being shown partially peeled back from the underlying shield to which it is mounted. This provides an additional benefit, in that the sheath member 34 can be made disposable.

Figure 3:
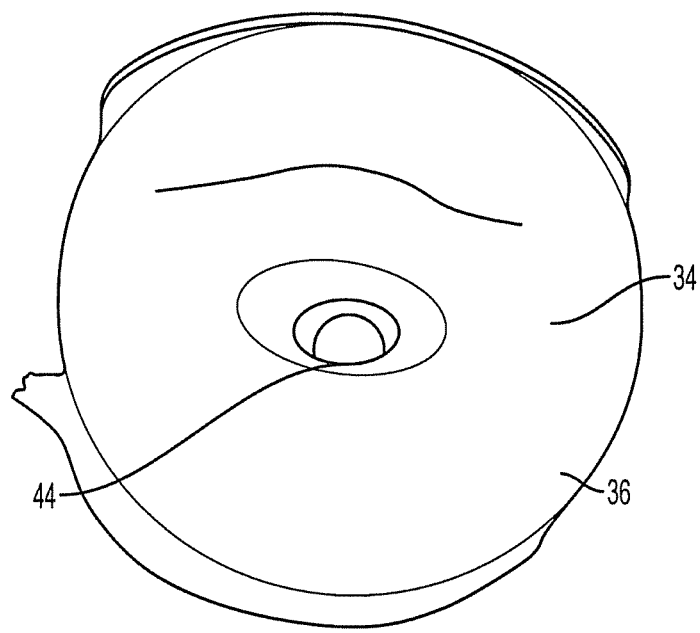
FIG. 3 is a front end view of the breastshield shown in FIG. 2.
Figure 4:
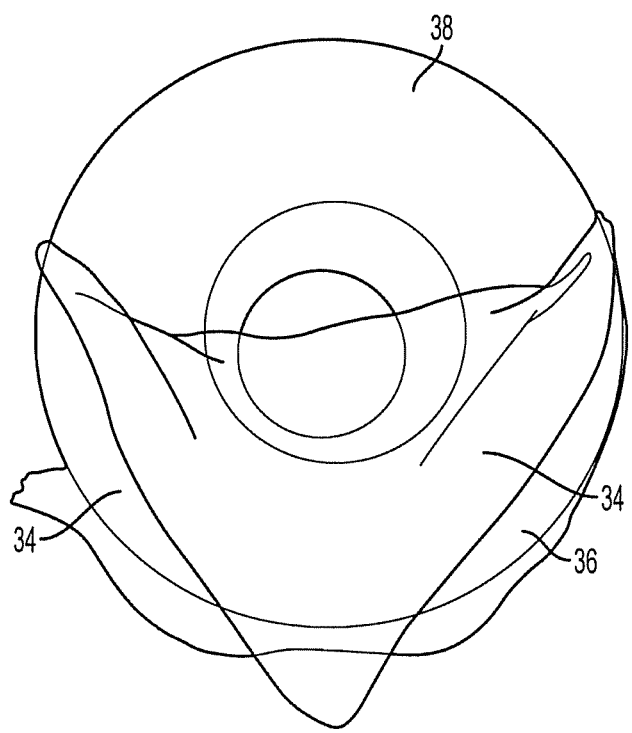
FIG. 4 is a front end view of the breastshield shown in FIG. 3, with a sheath partly detached from the breastshield.

Note that in this embodiment, the sheath member 34 yields a nipple receiving inner tunnel 44 which is out-of-round, i.e., not of a circular cross section (see FIG. 3). Here, it is somewhat elliptical. This provides a radial force to the nipple which tends to flatten the nipple on opposite sides, toward an elliptical shape.

It will be noted that FIG. 5 has a slightly different shape from that of FIGS. 1-4 in the area of the portion 26. This simply shows an application that is more of the traditional conical or funnel-shape for the breast-receiving part of the breastshield.

During expression, the breast, and primarily the nipple of the breast, is inserted into the mounted sheath member 34. Vacuum is applied from the vacuum source (pump) via the tube 20, with the vacuum conveyed to the breastshield by action of the barrier 14 within the clamshell-like chamber. The vacuum evacuates an antechamber 46 within the base 12, and is further conveyed into the space 48, thereby forming a plenum between the sheath member 34 and the inner sidewall 42 of the shield via a channel 50. As can be appreciated from FIGS. 2 and 5, the vacuum is thus applied on the distal end of the nipple via outward radial movement of the sheath member 34 as it expands, and through the valve 30. This in turn pulls upon the nipple constrained in the sheath member. This applies, in part, an outward force (referred to herein as "radial"). The sheath member 34 substantially limits the amount of air in the system. Essentially, there is only air initially located between the nipple and the valve that is involved, along with air in the antechamber 46.

Milk expressed into the downstream end of the sheath member 34 passes through the duckbill valve 30, where it is conveyed through internal conduit structure to the bottle 22. Note that the duckbill valve can be structured so that a preset vacuum level is maintained within the sheath member, such as at a minimum pressure (vacuum) of approximately −20 to −50 mmHg, for instance. A one-way duck bill valve 30 is used herein, but other equivalent types of valves can be used. Again, reference can be made to U.S. Publication No. 2008/0255503 regarding such a "baseline" vacuum concept and its effectuation.

Figure 6:
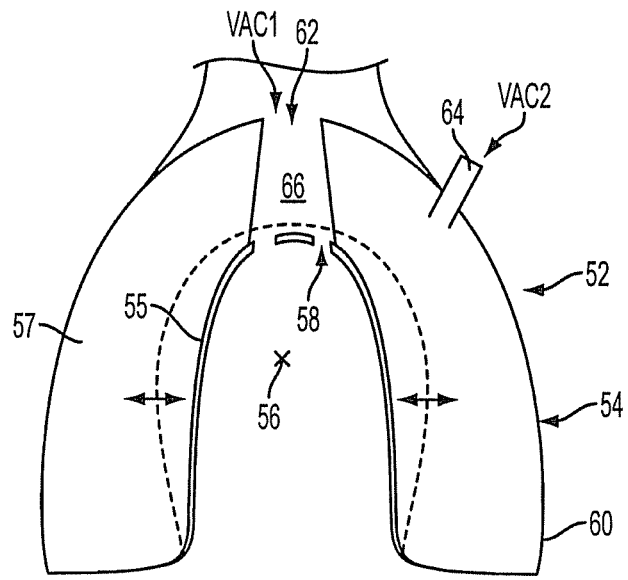
FIG. 6 is a schematic view in section showing another embodiment of the inventive breastshield using two sources of pressure (here, vacuum)

FIG. 6 is yet another embodiment of a system for expressing breastmilk that uses two sources of pressure, here vacuum. The system includes a breastshield 52 which would be attached to the base 12 of FIG. 1. Base 12 is part of a breastpump assembly more particularly shown in US Patent Publication 2008/0171970, described above with the first embodiment. Milk extracted in operation flows to the container 22 attached to a collar which communicates with conduit structure within the breastshield assembly. Again, the details of this breastshield assembly and breastpump can be gleaned from the foregoing patent application.

As can be seen in FIG. 6, this embodiment of the invention has a breastshield 52 with a receptacle portion 54, an inner side wall 55, a tubular extension or nipple tunnel 56, and a downstream end 66 with a plurality of openings 58. This embodiment has an outer sidewall 60 that is somewhat rigid (or relatively less collapsible than the inner sidewall 55, as will hereafter be made apparent). For example, the inner sidewall 55 could be similar to the foregoing sheath-like member 34. There is a first port 62, and a second port 64. The inner sidewall 55 includes the downstream end 66.

The first port 62 and the second port 64 are provided on the portion 54. The first port 62 is in communication with the antechamber 46 of the base 12, and a first vacuum source. The second port 64 is connected to a second vacuum source. The vacuum sources could be from a common vacuum generator and modulated, for instance, and need not be two separate sources.

The first vacuum evacuates the antechamber 46 within the base 12 (referring back to detail of the first embodiment), and is further conveyed through port 62 into the nipple tunnel 56 between the sidewalls of the breastshield 52. The first vacuum is applied to the breastshield 52 for a longitudinal force (axial) and for transporting the milk expressed from the nipple. Next, the second vacuum is applied from the second vacuum source, for radially pulling on the inner sidewall 55. This in turn radially pulls upon (or expands/decompresses) the nipple, which is constrained and embraced by the inner sidewall 55. Milk expressed into the downstream end 66 passes through the plurality of openings 58, where it is conveyed through internal conduit structure to the bottle 22.

As can now be seen, when a vacuum source is applied to the port 64 to yield a pressure less than that of in the nipple tunnel 56, the inner sidewall 55 expands, applying an outboard radial force to the encompassed nipple. When the vacuum levels near equilibrium, or the nipple tunnel goes more negative than the space 57, the resilient inner sidewall returns to its rest state or even compresses. It will be noted that this embodiment could so be adapted to apply an inboard force by having the vacuum between the sidewalls be such that the vacuum at first port 62 is greater than that between the sidewalls, thus in essence yielding a more "positive" pressure being applied about the nipple.

Here, again, the inner sidewall 55 substantially limits the amount of air in the system.

Those of skill in the art will appreciate the embodiment illustrated in FIG. 6 is not limited by the order the first vacuum source and the second vacuum source are applied to the breastshield 52. In an alternative embodiment, the second vacuum source is applied to the breastshield 52 before the first vacuum source is applied to the breastshield 52. In another embodiment, both the first vacuum source and the second vacuum source are simultaneously applied to the breastshield 52.

Figure 7:
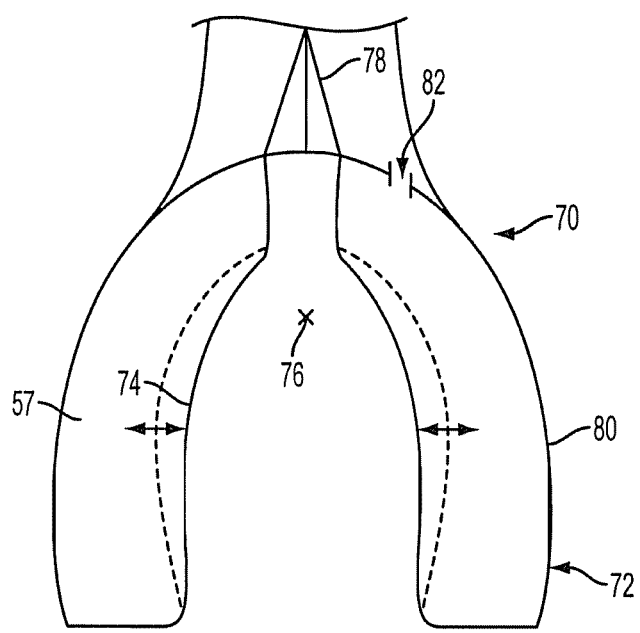
FIG. 7 is a schematic view in section of yet another embodiment of the inventive breastshield showing a system having a valve member capable of maintaining a baseline vacuum in the breastshield.

FIG. 7 is still another embodiment of a system for expressing breastmilk showing a system having a valve member capable of maintaining a baseline vacuum in the breastshield. As can be seen in FIG. 7, the breastshield 70 includes a receptacle portion 72, an inner sidewall 74, a tubular extension or nipple tunnel 76, a valve 78, an outer sidewall 80, and a vacuum inlet 82.

In the breastshield 70, the tubular extension 76 extends from the receptacle portion 72. The valve 78 is provided at the downstream end of the tubular extension 76, communicating with antechamber 46 of the base 12 (again, refer to the base and related structure of FIGS. 1 and 5). The vacuum inlet 82 is between the antechamber 46 and the space 57 between the sidewalls.

The inner sidewall 74 is, at its downstream end of the tubular extension 76, sealed about the upstream end of the valve 78, which here is a duckbill valve. As in the embodiment of FIG. 6, the inner sidewall 74 is pulled away from the nipple when a vacuum is applied between the sidewalls which is more negative (greater vacuum) than that in the nipple tunnel 76.

Of course, this is simply a function of pressure (or force) differential as between the tubular extension and the space 57. Those with skill in the art will recognize many ways to generate the desired pressure or force differential for movement of the inner sidewall 74 besides what has been specifically described with respect to FIGS. 6 and 7.

In operation, the inner sidewall 74, which is preferably made of silicone rubber in a relatively thin thickness, receives the nipple of a breast and snugly holds the nipple and some adjacent breast in a supple embrace.

Vacuum is applied from the vacuum source, which is preferably a pump, via the tube 20, with the vacuum conveyed to the breastshield both at the antechamber 46 (downstream of the valve 78) and at the inlet 82. While a common negative pressure is being applied both downstream of the valve 78 and at the inlet 82, the valve 78 is designed to operate such that the vacuum in the space 57 between the sidewalls goes more negative than that in the nipple tunnel for a brief period. This applies the radial pull on the nipple, as the nipple tunnel 76 expands. Ultimately, the vacuum pressure causes the valve 78 to open, so milk passes through the valve 78, and is transported to the milk container 22.

Various breastshields disclosed herein may be used with a vacuum pump as shown and described in a PCT application no. PCT/CH2010/000225, entitled "Device and Method for Expressing Human Breastmilk," filed on Sep. 17, 2010. Vacuum pumps for use in breastpumping are, however, well known.

The valve 78 also can serve to yield a baseline vacuum being maintained in the nipple tunnel 76, closing at a predetermined negative pressure, as previously described with relation to the first embodiment above. A baseline vacuum would be one that is maintained during some or all of a pumping session, such that the vacuum seen at the nipple does not return to ambient, but remains at, say, a pressure of approximately −20 to −50 mmHg, before returning to a greater vacuum during milk extraction. Those skilled in the art will appreciate the benefits of maintaining a baseline vacuum during operation. For example, milk expression should be more comfortable to the mother.

Figure 8:
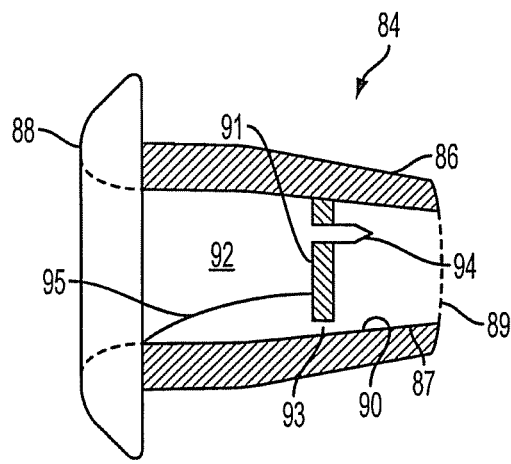
FIG. 8 is yet another embodiment of the inventive breastshield in sectional view.
Figure 9:
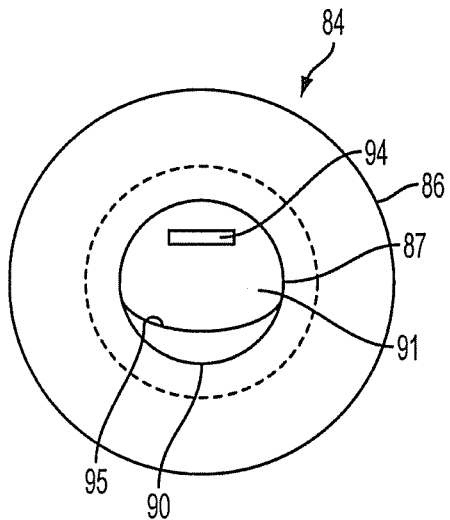
FIG. 9 is a front end view of the breastshield of FIG. 8.
Figure 10:
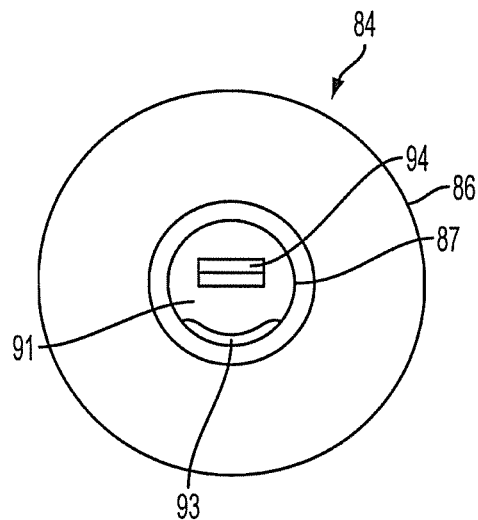
FIG. 10 is a rear end view of the breastshield of FIG. 8.

FIGS. 8 through 10 show yet another embodiment of a system for expressing milk. The breastshield 84 is preferably molded in silicone, in large part, and is somewhat flexible. It has an outer wall 86, an inner wall 87, an upstream turned out rim 88 forming an opening, a downstream end 89, and an inner sidewall 90. A tubular extension or nipple tunnel 92 is thereby defined. A valve 94 is mounted on a dividing wall 91, which extends transversely across the nipple tunnel, at a point where the nipple will preferably not impact the wall in any deleterious manner during pumping. The downstream end 89 connects to the antechamber 46 of the base 12, for example (see FIGS. 1 and 5 regarding the base 12 and related structure).

Inboard of the sidewall structure 90 is a thin flexible member 95, which extends across a quadrant of the upstream part of the nipple tunnel, in front of the wall. The thin flexible member 95 at its downstream end is sealed to the dividing wall 91. This creates a bladder structure or member, which is preferably designed to be reminiscent of the tongue of a baby. There is a slot 93 in the wall 91 which communicates with the interior of the foregoing bladder. The slot 93 conveys vacuum pressure to the bladder interior. While a slot 93 is shown, it could be greatly expanded in this area, for ease in manufacturing.

Reminiscent of the embodiment of FIG. 7, a negative pressure (vacuum) applied at the end 89 initially generates a pressure differential between the area of the nipple tunnel 92 within which the nipple is received and surrounded, and the interior of the bladder. This causes the member 95 to move radially outboard (or outward) relative to the nipple and the breast. This in turn pulls the nipple outwardly, and then contracts when the member 95 returns to its initial position. Responsive to this action, the nipple expresses milk. Milk expressed into the downstream end of the tubular extension 92 passes through the valve 94, which is preferably a duckbill valve, where it is conveyed through internal conduit structure to the bottle 22. Note that these types of breastshield shapes of FIGS. 6-10 for instance, serve to best position the nipple therein, thereby further facilitating a minimization of any residual air volume.

Figure 11A:
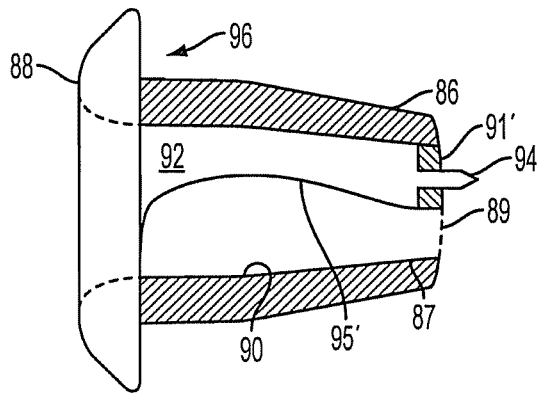
FIG. 11A is a modified version of the embodiment of FIG. 8.

Turning now to FIG. 11A, this is a modified version of the breastshield of FIGS. 8 through 10. This breastshield 96 has a member 95' that radially extends farther into the tubular extension 92 than the member 95 of breastshield 84 of FIG. 8. Dividing wall 91' is moved more downstream, with its duckbill valve 94.

Figure 11B:
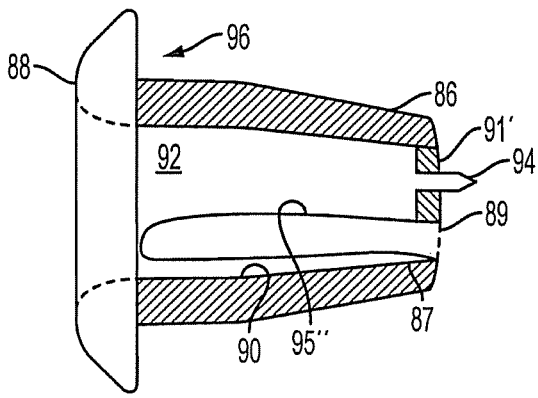
FIG. 11B is another modified version of the embodiment of FIG. 8.

FIG. 11B is a variation of what has been described with respect to FIG. 11A. Here, the bladder or tongue member 95" is now separated from the sidewall structure 90, and is much more like the forward part (free end) of a baby's tongue. What is particularly novel with this embodiment is that, when negative pressure (vacuum) is released downstream of the breastshield 96 (upon completion of the vacuum cycle), member 95" actually initially expands within the extension 92 (given the pressure differential that then exists between the member and the interior of the extension 92). Note that the embodiment of FIG. 11A could also provide this feature.

FIGS. 12 and 13 illustrate still another embodiment of a system for expressing milk. This time, the breastshield 98 assumes a relatively rigid more funnel-shaped construct, with a receptacle portion 100 having a more traditional circular cross section nipple tunnel 101 downstream thereof. There is an inner side wall 102 to the funnel, an upstream edge or rim 104 defining the widened opening for the portion 100, and a downstream end 105.

Fitted inside of the funnel is a flexible liner 106, which can be a sheath-like member previously described. Liner 106 has a rim 107 which is formed with an outer lip that is turned inwardly to form an annular channel around the circumference of the rim 107. This channel is designed to more or less snap fit around the rim 104 of the conical portion, to fix the liner 106 at the upstream end. At the downstream end of the liner 106, a knob 112 is formed. That knob 112 fits through an aperture of an endwall 109 that extends across the end 105 of the nipple tunnel, and is thereby held in place. The spacing between the rim 104 and the endwall attachment of the liner 106 is such that the liner 106 may be, or preferably is stretched, and pulled taut when attached within the funnel. The shape of the liner 106 is also funnel-like, but results in a space (plenum) 108 being formed between the inner sidewall 102 of the funnel and the outside of the liner 106. Note that the downstream end 105 has a plurality of slots 111 for fluid conveyance (fluid being both milk and vacuum). The liner 106 includes one (or more) lateral openings 110 at the knob 112, which operates much like the foregoing duckbill valves.

In operation of the breastshield 98, liner 106 is mounted inside of the funnel (portion 100 and nipple tunnel 101) so that sidewalls of the liner 106 are pulled away from the inner sidewall 102. The nipple and breast placed in the liner 106 are thus closely embraced. The vacuum is applied from the vacuum source, which is preferably a pump, via the tube 20, with the vacuum conveyed to the breastshield 98. The vacuum causes the liner 106 to expand into the space between the inner sidewall 102, in turn applying a radial outward force to the nipple. Milk expressed into the downstream end of the sheath-like member 106 passes through the lateral opening 110 where it is conveyed through the plurality of slots 111 of the endwall 109, then through internal conduit structure to the bottle 22.

FIGS. 14 and 15A show yet another embodiment of a system for expressing breastmilk. The system includes a breastshield 114 which is funnel-shaped, having a receptacle portion 116, from which extends a somewhat tubular extension or nipple tunnel having a first part 124. This nipple tunnel is formed as an extensible chamber, however, with another part indicated at 128. The function of this extensible nipple tunnel will shortly be described.

Located within the receptacle portion 116 and extending into the nipple tunnel is an inner liner part 126. The inner liner part 126 is fixed at its upstream end to the inner wall of the receptacle portion. Its downstream end 132 extends inboard from the sidewall, and is spaced from the walls defining the tubular extension. Its downstream end 132 has a plurality of openings 138 for fluid flow.

There is a duckbill valve 122 connected to the nipple tunnel. That valve communicates with conduit structure leading to a milk container, or could directly pass to the bottle.

There is a hinge-like structure 130 formed as a bend between the two parts of the nipple tunnel 124, 128. The distal end of the nipple tunnel is closed at 120, with a knob formed thereon. With an axial force applied to the knob 120 to move it toward (direction 136) and then away from (direction 134) the distal end of the liner part 126 (thereby reciprocating part 128 of the nipple tunnel), the volume of the nipple tunnel 124, 128 is caused to contract and expand. This initially generates an intermittent vacuum (negative pressure) within the breastshield 114 (more so in the area around the nipple).

The nipple is constrained in the liner part 126 within the nipple tunnel. Milk expressed by this reciprocating action flows through the openings 138, into the nipple tunnel 124, 128 and then through the valve 122. FIG. 15A illustrates the nipple tunnel being compressed in the direction 136. After milk is expressed, it collects in the nipple tunnel 124, 128. On the next stroke, the milk is pushed through the valve 122, which is preferably a duckbill valve, where it is conveyed through internal conduit structure to the bottle 22.

Of further interest in this embodiment is that the milk thereby replaces the initial working fluid of the reciprocating pump formed by the expansible nipple tunnel, going from air to milk (liquid). The system thus goes from pneumatic system to a hydraulic system, increasing efficiency. Moreover, the mother's own milk can now be used to warm the breastshield 114, which makes the mother more comfortable during milk expression, and research has demonstrated increases milk flow rate.

Figure 15B:
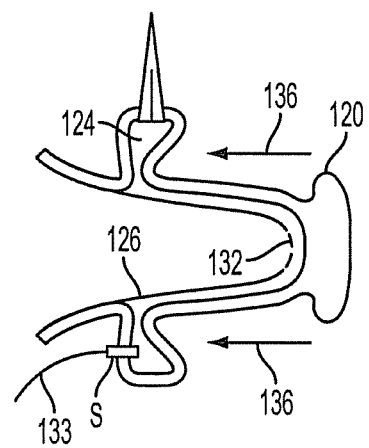
FIG. 15B is a view like that of FIG. 15A, showing the valving in an inverted (upward) position, and with a pressure sensor.

In this embodiment, we now can see how the air or "dead volume" is virtually eliminated within the entire system. FIG. 15B is intended to further show this, illustrating how the valve 122 can be oriented upwardly (relative to ground), or in virtually any other position, since gravity is no longer the prime (or only) mover of the milk. Tubing or other conduit structure (not shown) would surround the valve 122, for example, to convey milk to a container. Milkflow is thus effected by the pumping action of the reciprocating parts of the nipple tunnel 124, 128, and is independent of gravity. This by itself is considered to be a highly significant advance in breastpumping. The entire breastpump assembly has furthermore become extremely compact and efficient.

FIG. 15B also illustrates the additional feature of applying a pressure sensor S to the system. This sensor would be used to monitor the pressure being applied at the nipple providing a signal to a controller via electrical connection 133, for setting a desired maximum pressure for instance, or perhaps as well a desired minimum (referring back to the "baseline" pressure concepts discussed above). Use and application of such a pressure sensor or pressure transducer is disclosed in U.S. Publication No. 2008/0255503.

Figure 21:
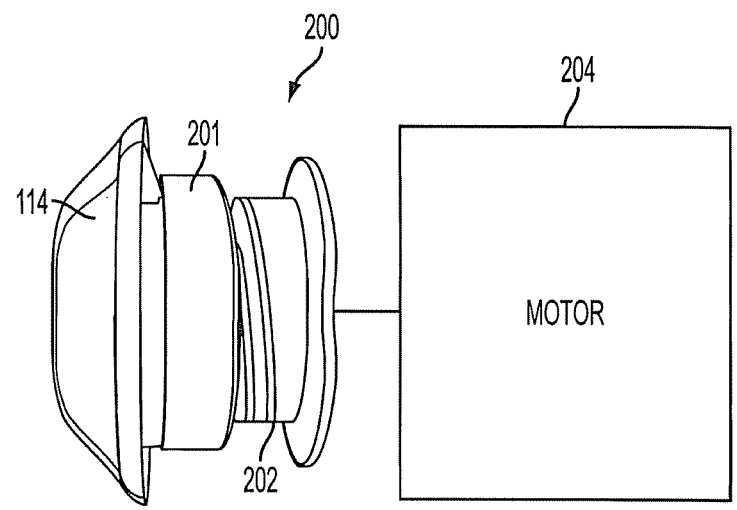
FIG. 21 is a schematic of a drive mechanism for use with the breastshield shown in FIG. 14.

The breastshield 114 disclosed in this embodiment would use a rotary drive mechanism 200, such as in FIG. 21. The drive mechanism 200 has a ring 201 within which the breastshield 114 is maintained. Ring 201 has internal threads. Received within the ring 201 is a rotary drive member 202, which is externally match-threaded to the ring 201. A conventional motor 204 is schematically illustrated, and connects through a conventional drive train to the drive member 202 to thereby rotate the drive member 202, relative to the ring 201. The knob 120 of the breastshield 114 is mounted within an orifice of the drive member 202. When the drive member 202 is turned in one direction, it moves outwardly relative to the ring 201, thereby extending the nipple tunnel 124, 128. When drive member 202 is rotated in the opposite direction, it moves inwardly relative to the ring 201, compressing the nipple tunnel.

Figure 22:
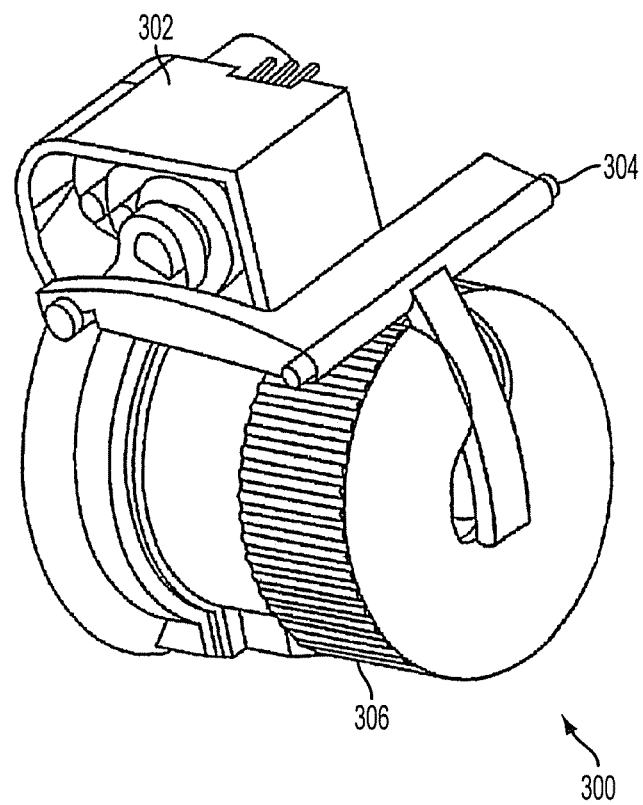
FIG. 22 is another example of a drive mechanism for use with the breastshield shown in FIG. 14.

Another example of a drive mechanism which may be used with the breastshield 114 and substantially eliminate "dead volume" throughout the entire system is shown in FIG. 22. This type of drive mechanism may include a piston lever arm system 300, and is further described in U.S. Pat. No. 7,223,255, issued on May 29, 2007, entitled "System for a Portable Hands-Free Breast Pump and Method of Using the Same," which is herein incorporated by reference in its entirety. The breastshield 114 would be adapted to fit the general makeup of the piston lever arm system 300. The knob 120 of the breastshield 114 connects to a piston cylinder 306. The piston lever arm system 300 includes a servomotor mechanism 302 connected to a lever arm 304. The lever arm 304 is used to adjust the piston cylinder 306. The servomotor mechanism 302 pivotally moves the lever arm 304, which then linearly moves the piston cylinder 306 to move the knob 120, in and out in a linear fashion, to thereby extend and compress the nipple tunnel 124, 128.

Figure 16:
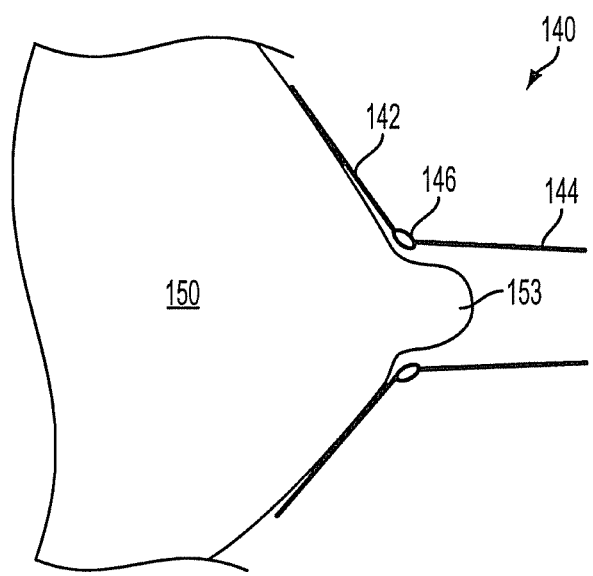
FIG. 16 is still another embodiment, this one shown schematically in section and elevation.
Figure 17:
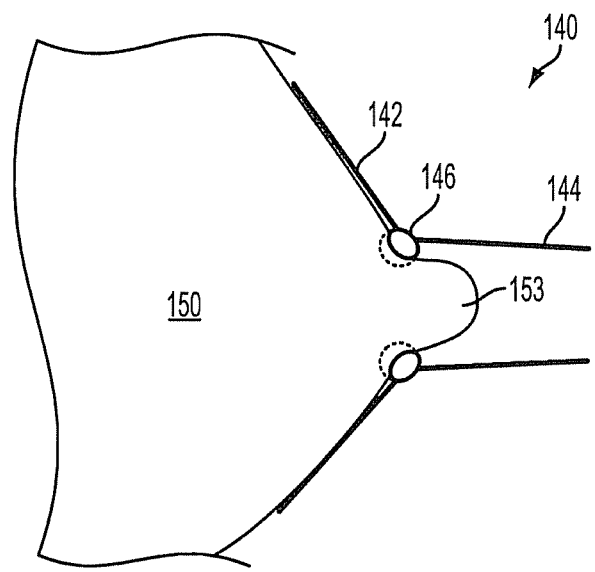
FIG. 17 is the embodiment of FIG. 16, with a nipple ring being enlarged.

FIGS. 16 and 17 illustrate still another embodiment of a system for expressing breastmilk. The breastshield 140 includes an upstream cone 142, a nipple tunnel 144, and an inflatable chamber or bladder 146. The cone 142 and nipple tunnel 144 yield a funnel-shape.

As can be seen in FIG. 16, the inflatable chamber 146, which is preferably toroidal, is coupled to the cone 142 and the nipple tunnel 144 at substantially the area of transition in the funnel to the nipple tunnel 144. The nipple tunnel 144 is in communication with a vacuum source (not shown). The inflatable chamber 146 is in communication with a pressure source (not shown).

In operation, the funnel receives the nipple 153 of a breast 150 and snugly holds the nipple 153 and some adjacent breast. In this embrace, the distal end of the nipple 153 extends into the nipple tunnel 144. Next, as can be seen in FIG. 17, the inflatable chamber 146 expands and grows in size. The inflatable chamber 146 preferably expands in response to a pressure applied by the pressure source. When expanded, the inflatable chamber 146 contacts the breast. The inflatable chamber 146 preferably contacts the breast at substantially the area of transition from the areola to the nipple 153. The nipple 153 further extends into the nipple tunnel 144 in response to the breast being contacted by the inflatable chamber 146.

Next, a vacuum is applied by the vacuum source, which the nipple tunnel conveys to the nipple 153. The nipple surface area that the vacuum is conveyed to is minimized when the inflatable chamber 146 contacts the nipple (and any adjacent breast). In response to the vacuum action, the nipple 153 expresses milk. The milk flows through the nipple tunnel 144 and through a conduit structure to a container (not shown). Minimizing the breast area and surrounding open volume that the vacuum must interact with increases efficiency.

Figure 18:
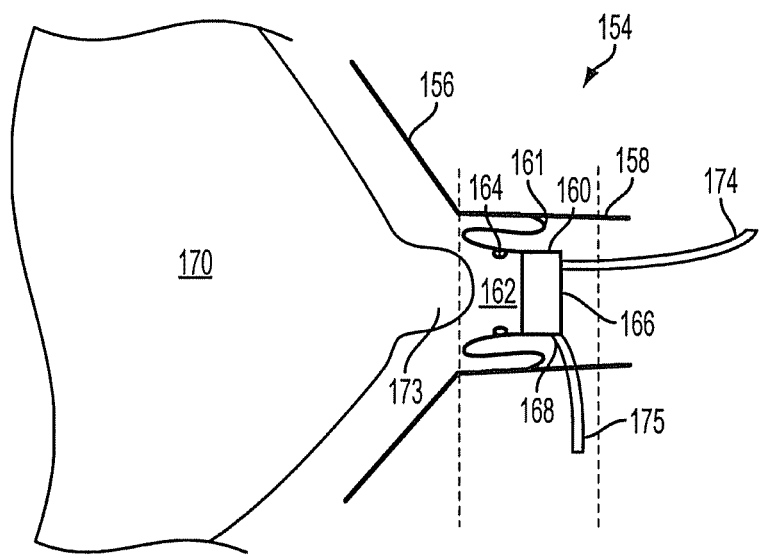
FIG. 18 is a figure similar to that of FIG. 16 of an embodiment having a nipple cap carried by a movable wall.
Figure 19:
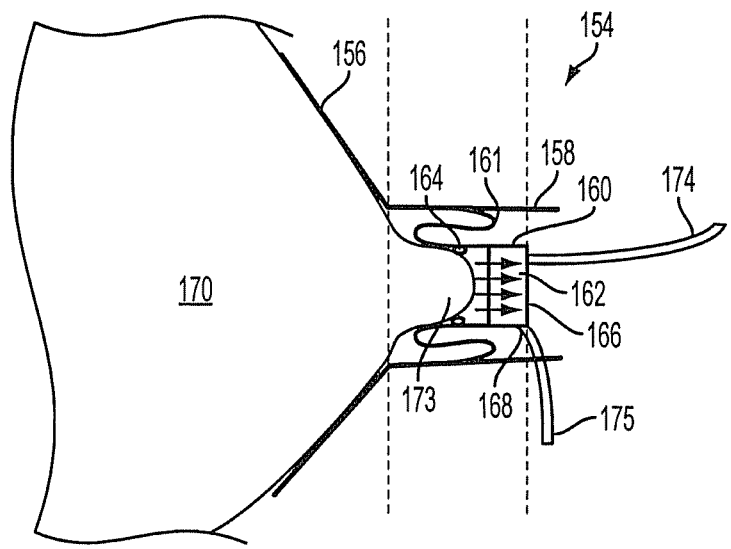
FIG. 19 is the embodiment of FIG. 18 with the nipple cap attached about the nipple.

FIGS. 18 and 19 show yet another embodiment of a system of expressing milk. The breastshield 154 includes a cone 156, a nipple tunnel 158, and a flexible membrane 161. The flexible membrane 161 is preferably folded upon itself. A cup 160 has a sealing ring 164, a distal or downstream end 166, and an opening 168.

In the breastshield 154, the cone 156 and nipple tunnel 158 define a funnel shape. The nipple cup 160 is in communication with a vacuum source (not shown). The flexible membrane 161 is located in the nipple tunnel 158. Membrane 161 is connected to the nipple cup 160, and is also connected to the nipple tunnel inner wall. Due to the connections of the stretchable membrane 161, the stretchable member is configured to move in the nipple tunnel 158. The sealing ring 164 is connected to the nipple cup 160. The sealing ring 164 is located inside the nipple cup 160 upstream of both the distal end 166 and the opening 168. The opening 168 is connected to an internal conduit structure, which is in turn is connected to a container (not shown), for milk flow. A one-way valve (not shown) may be placed at or beyond opening 168 to provide one-way air or milk flow through the tubing 175.

In operation, the funnel receives the nipple 173 of a breast 170 and snugly holds the nipple 173 and the adjacent breast. The nipple 173 extends into the area 162 within the nipple cup 160. The nipple cup 160 can expand both laterally and radially to receive the nipple 173. The nipple cup 160 expands to receive the nipple in response to the translation of the flexible, preferably stretchable, membrane 161 within the nipple tunnel 158. Due to the translation of the membrane 161, the nipple cup 160 is configured to receive nipples of varying diameter and varying length, thereby minimizing system volume.

As can be seen in FIG. 19, the distal end of the nipple 173 extends past the sealing ring 164. In this configuration, the flexible membrane 161 laterally seals the nipple 173, which minimizes the nipple surface area to which a vacuum force is to be applied.

Next, a vacuum may be applied by the vacuum source through a hose or tube 174, and the vacuum is conveyed to the distal end 166 of the nipple cup 160. In response to the vacuum, the nipple cup 160 applies a force to the nipple 173. In response to the applied force, the nipple 173 expresses milk, and the milk flows through the opening 168 into tubing 175 and through the internal conduit structure to the container.

Figure 20:
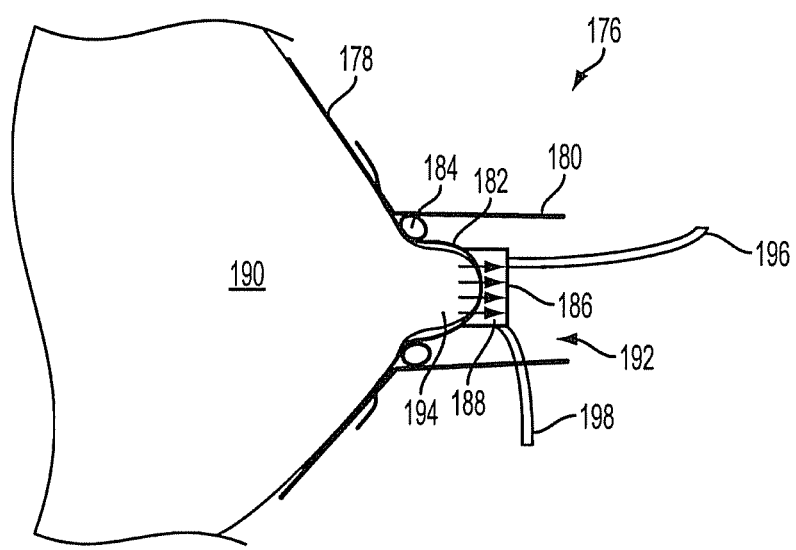
FIG. 20 is yet another embodiment using a figure like that of FIG. 18, employing a nipple cap and a nipple cover.

FIG. 20 is still another embodiment of a system for expressing breastmilk. The breastshield 176 includes an upstream cone 178, a downstream nipple tunnel 180, nipple cover 182, a collar 184, and a cap 186. The cap 186 includes an opening 188. The cap 186 is much like that previously described with respect to the embodiment of FIGS. 18 and 19.

In the breastshield 176, the nipple cover 182 is attached at its upstream end to the cone 178, and the nipple cover 182 extends into the nipple tunnel 180. The collar 184 is located around the nipple at its base and functions much like an O-ring. The collar 184 is preferably connected to the inner wall of the nipple tunnel 180. The cap 186 is connected at its upstream end to the nipple cover 182. The opening 188 is located on the cap 186, and the opening 188 is connected to tubing 198 and then to an internal conduit structure, which is in turn connected to a container (not shown), for milk flow. Alternatively, the milk outflow could go directly into a container. A one-way valve (not shown) may be placed at or beyond opening 188 to provide one-way air or milk flow through the tubing 198.

In operation, the funnel receives the nipple 194 of a breast 190 with the nipple 194 extending into the cap 186. In this configuration, the nipple cover 182, which is preferably a plastic film that is fluid permeable, or which has small openings in it, covers the nipple 194, and the collar 184 closes the nipple cover 182 against the breast. The collar 184 preferably contacts the breast 190 at substantially the area of transition from the areola to the nipple 194. When the vacuum source applies a vacuum through tube 196, the vacuum generates a force applied to the nipple covered by the nipple cover 182. In response to the applied force, the nipple 194 expresses milk. As can be seen in FIG. 20, the milk flows through the nipple cover 182 to the opening 188.

While certain features and embodiments of the present application have been described in detail herein, it is to be understood that the application encompasses all modifications and enhancements within the scope and spirit of the following claims.

The invention claimed is:

1. A breastshield assembly comprising:
   a structure for receiving a nipple therein;
   a nipple tunnel in communication with the structure;
   a valve connected to the nipple tunnel; and
   a liner part formed within the nipple tunnel, the liner part including a plurality of openings at a downstream end;
   wherein a volume of the nipple tunnel is configured to expand and contract in response to a pressure applied by a pressure source to generate a vacuum within the breastshield assembly, which causes the nipple to express milk;
   wherein the expressed milk flows through the plurality of openings in the liner, and collects in the nipple tunnel, thereby replacing the pressure applied by the pressure source with the expressed milk and creating a hydraulic system which generates subsequent pressure in the breastshield assembly.

2. The breastshield assembly of claim 1 wherein the valve is oriented upwardly with respect to the nipple.

3. The breastshield assembly of claim 1 wherein the downstream end of the nipple tunnel is closed and coupled to a knob configured to be acted upon by an axial force.

4. The breastshield assembly of claim 1 wherein the nipple tunnel has a hinge in the form of a bend between a first part and a second part of the nipple tunnel, thereby permitting a volume of the nipple tunnel to contract and expand.

5. A wearable breastpump assembly comprising:
   a housing;
   a breastshield part located within the housing within which at least a nipple of a nursing mother is received, the breastshield part having an inner liner configured to surround and embrace the nipple, the inner liner including a plurality of openings at one end;
   a valving device communicating with the breastshield part;
   a drive mechanism located within the housing;
   conduit structure communicating with the breastshield part conveying expressed milk from the breastshield part, and conveying pressure from the drive mechanism to the nipple; and
   a container within which expressed milk is received from the conduit structure;
   wherein the drive mechanism is configured to cause a volume of the nipple tunnel to contract and expand to initially generate a negative pressure through the use of air as an initial working fluid, causing milk to be expressed, after milk is expressed, the expressed milk collects in the nipple tunnel thereby replacing the initial working fluid with the expressed milk and creating a hydraulic system which generates subsequent pressure in the breastshield.

6. The breastpump assembly of claim 5 wherein a downstream end of the nipple tunnel is closed and coupled to a knob configured to be acted upon by an axial force.

7. The breastpump assembly of claim 5, wherein the housing has a ring-shape.

8. The breastpump assembly of claim 5 wherein the valving device is oriented upwardly with respect to the nipple.

9. The wearable breast pump system of claim 5 further comprising a container within which expressed breast milk is received, wherein the container is located anywhere other than downwardly with respect to the nursing mother's breast.

10. A wearable breast pump system comprising:
    a housing with a self-contained pumping mechanism;
    a breastshield located within the housing within which at least a nipple of a nursing mother is received; and
    a nipple tunnel having a top and bottom surface communicating with the breastshield;
    a valving device coupled to the top surface of the nipple tunnel: and a liner configured to surround the nipple, the liner including a plurality of openings at one end; and
    wherein fluid is configured to pass through the valving device against gravity when the valving device is oriented upwardly.

11. The wearable breast pump system of claim 10 wherein the nipple tunnel is configured to expand and contract in response to a pressure applied by the pumping mechanism to generate a vacuum within the breastshield, which causes the nipple to express milk.

12. The wearable breast pump system of claim 10 further comprising a container within which expressed breast milk is received, wherein the container is located anywhere other than downwardly with respect to the nursing mother's breast.

* * * * *